(12) United States Patent
Pauli

(10) Patent No.: US 6,442,777 B1
(45) Date of Patent: Sep. 3, 2002

(54) PATIENT SUPPORT FOR A DIAGNOSTIC RADIOGRAPHY SYSTEM

(75) Inventor: Karlheinz Pauli, Neunkirchen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/614,543

(22) Filed: Jul. 12, 2000

(30) Foreign Application Priority Data

Jul. 16, 1999 (DE) .......................... 199 33 802

(51) Int. Cl.[7] .................. A61G 13/00; A61G 13/12
(52) U.S. Cl. .............................. 5/601; 5/622
(58) Field of Search ................... 5/601, 622, 621; 378/209; 600/415

(56) References Cited

U.S. PATENT DOCUMENTS 4,616,814 A * 10/1986 Harwood-Nash et al. ...... 5/601
4,688,780 A * 8/1987 Hanz ............................. 5/621
5,233,713 A * 8/1993 Murphy et al. ................. 5/601
5,640,958 A * 6/1997 Bonutti ......................... 5/601
5,724,970 A * 3/1998 Votruba et al. ................ 5/601

* cited by examiner

Primary Examiner—Alexander Grosz
(74) Attorney, Agent, or Firm—Schiff Hardin & Waite

(57) ABSTRACT

A support device for a diagnostic radiography system has a support plate with a portion for supporting a first region of an examination subject and a support element for a second region of the subject. The support element is connected to the support plate such that it can be adjusted by an adjusting mechanism that is arranged on the side of the support element that faces away from the portion of the support plate that is provided for accepting the first region of the examination subject.

9 Claims, 2 Drawing Sheets

PATIENT SUPPORT FOR A DIAGNOSTIC RADIOGRAPHY SYSTEM

BACKGROUND OF THE INVENTION

1. Field of the Invention

The present invention relates to a bearing device for a diagnostic radiography system of the type having a support plate with a portion for accepting a first region of an examination subject and a support element for a second region of the subject, the support element being connected to the support plate such that it can be adjusted by an adjusting mechanism.

2. Description of the Prior Art

Support devices such as this are used in computed tomography (CT) systems, for example, where they serve for accepting human patients. There, the portion of the support plate that is provided for supporting the first region of the examination subject is designed as a support for the body of the patient, and the support element is designed as a head support. To guarantee the adjustability of the head support relative to the support plate, the two parts are connected by a hinge, which can be locked when the desired incline has been set. Since the hinge is under heavy load, it must be produced from materials that are very sturdy and thus very dense. This leads not only to artefacts in the tomograms, which are generated by means of the CT system, of a patient reclining on the support plate, but also to disturbances in shadow images, known as topograms, which are commonly prepared prior to the actual computed tomography process in order to be able to localize an area of the patient of which to generate the tomograms. The imaging of the hinge in such a shadow image can render it unusable.

The risk of the occurrence of artefacts in the shadow images or the occurrence of superposed attenuation in the X-ray images, can be reduced by mechanical constructions utilizing expensive plastics, however, this solution is not satisfactory to medical personnel. Also, the lack of adjustability of the head support relative to the support plate is seen as unacceptable by medical workers.

SUMMARY OF THE INVENTION

An object of the present invention is to design a support device of the type described above wherein the adjustability of the support relative to the support plate is guaranteed without a consequent reduction of the diagnostic value of the X-ray images that are generated from an examination subject who is located on the support plate.

This object is inventively achieved in a support device for a diagnostic radiography system which has a support plate with a portion for supporting a first region of an examination subject and a support element for a second region of the subject, wherein the support is connected to the support plate such that it can be adjusted by an adjusting mechanism which is arranged on the side of the support faces away from the section of the support plate which is provided for accepting the first region of the examination subject.

In contrast to conventional devices, the adjusting mechanism in the inventive device is not located between the section of the support plate that is provided for supporting the first region of the subject and the support element for the second region of the subject; rather, it is arranged on the other side of the support element, and thus on the other side of the second region of the subject, as seen from the section of the support plate that serves for supporting the first region of the subject. It is thus clear that, as a rule, it is not possible for an image of the adjusting mechanism to be superimposed in an image of an examination subject, nor for it to cause artefacts in tomographic imaging of the subject.

The adjusting mechanism, by means of which the support is preferably attached to the support plate such that it can be swivelled about an axis extending essentially transverse to the longitudinal axis of the support plate, can be attached to the support plate permanently or detachably according to different variants of the invention. In the case of a detachable attachment of the adjusting mechanism, a screw connection can be provided, though a plug connection may be advantageous for more comfortable handling.

According to variants of the invention, to guarantee adjustability of the support relative to the support plate, the adjusting mechanism can have an articulated joint for adjusting the angle of the support element relative to the support plate and/or an arrangement for adjusting the height of the support element relative to the support plate. In a preferred embodiment of the invention, a push-pivot joint is provided, which can be displaced on a carrier extending essentially perpendicular to the support plate for height adjustment and which connects the support to the carrier in a pivoting manner for adjustment of the inclination.

In the case where the support device is provided for a patient, the section of the support plate that is provided for supporting the first region of the examination subject is fashioned as a support for the body of the patient, and the support element is fashioned as a head support The inventive bearing mechanism is preferably provided for a CT system.

DESCRIPTION OF THE PREFERRED EMBODIMENTS

Figure 1:
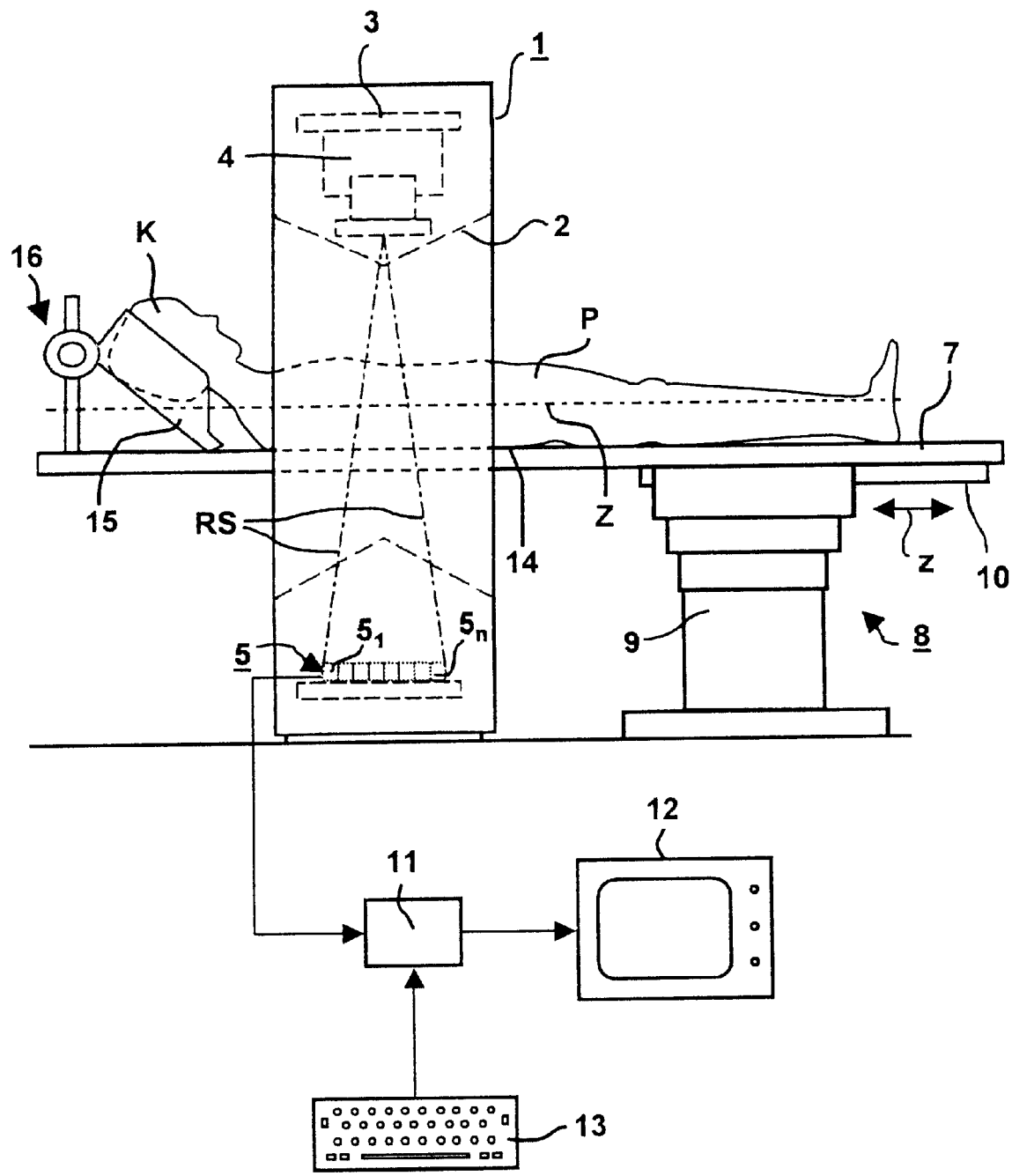
FIG. 1 shows a diagnostic radiography system, namely a computed tomography (CT) system, with an inventive support mechanism.

FIG. 1 shows a CT system having gantry 1 with a measuring opening which is surrounded by a rotating ring 3, on which an X-ray source 4 and a detector system are attached. The detector system has a detector 5 which is constructed in known fashion as an arc that curves about an axis extending through the focus of the X-ray source 4, preferably parallel to a system axis z. The detector 5 has several lines $5_1$ to $5_n$ of detector elements, each of which forms one row of detector elements. A pyramidal X-ray beam, which is represented by a dotted line RS, emanates from the X-ray source 4 and strikes on the detector 5.

The gantry 1 with the X-ray source 4 and the detector 5, and at least the support plate 7, which is provided for accepting an examination subject such as a patient P, of a bearing device (referenced 8 overall) can be adjusted relative to one another in the direction of the longitudinal axis of the support plate 7, which extends parallel to the system axis z, by means of a motorized drive (which is not illustrated). In the case of the CT system in FIG. 1, this is achieved by mounting the support plate 7 to the base 9 of the support device 8, such that it can be displaced by a carrier 10 in the direction of the system axis z of the support plate 7; that is, in the direction of the double arrow z.

The support plate 7 is produced from a material with a weak attenuating effect on X-radiation, for instance carbon fiber reinforced plastic (CFRP) or wood.

To register CT pick-ups, the gantry 1 and the support plate 7 are moved relative to one another into a position in which the support plate 7 extends through the measurement opening 2 of the gantry 1, and the patient P lying on the support plate 7 assumes a position relative to the gantry 1 such that a region of the patient P that is to be examined is covered by the X-ray beam RS.

To register pick-ups of one or more planar slices of the patient P, the rotating ring 3 with the X-ray source 4 and the detector 5 is rotated around the system axis z in order to pick up a number of projections of different directions, which serve for the reconstruction of one or more tomograms of one or more planar slices of the patient P, while the gantry 1 and the support plate 7 maintain their positions relative to one another with respect to the direction of the system axis z. Since the detector 5 has several lines of detector elements, it is possible simultaneously to register projections relating to a maximum number of slices of the patient P corresponding to the number of rows $5_1$ to $5_n$ of the detector. The measurement values which correspond to the projections and which originate at one or more lines $5_1$ to $5_n$ of the detector 5 are fed to a computer 11, which computes one or more tomograms from these measurement values in known fashion, which can be displayed on a display device such as a monitor 12. A keyboard 13 is connected to the computer 11 for operating the CT system.

To perform a scan of a type known as a spiral scan, with the X-ray source 4 active (i.e. emitting X-rays) the support plate 7 is displaced linearly in the direction of the system axis z (i.e. in direction z) with continuous rotation of the rotating ring 3, so that the registered projections relate not to one or more planar slices, but instead to one or more helix-shaped slices. Using known methods for spiral interpolation, it is possible to calculate computed projections relating to one or more desired planar slices from the measured projections obtained in the course of the spiral scan, which computed projections permit reconstruction of corresponding tomograms. Beyond this, it is possible to reconstruct three-dimensional images on the basis of spiral scans, since not only a planar slice, but also a volume, is scanned in the course of a spiral scan.

In order to be able to specify the region of the patient P which is to be covered in the examination prior to performing computed tomography pick-ups, either with a stationary or moving support plate 7, an X-ray shadow image is typically prepared in that the patient P is moved through the measurement opening 2 by pushing the support plate 7 in the direction z, and the X-ray source 4 is simultaneously activated without the rotary ring 3 rotating. The computer 11 then creates an X-ray shadow image from the measurement values delivered by the detector 5.

With the aid of this X-ray shadow image, it is possible prior to a spiral scan to specify the region of the patient P that is to be scanned in the course of the spiral scan. In the case of conventional computed tomography pick-ups, it is possible to position the patient P in the measurement opening 2 with the aid of the X-ray shadow image such that a region that is to be examined is covered by the X-radiation.

The support plate 7 of the inventive support device 8 has a support portion 14 which serves for supporting a first region, namely the torso and extremities, of the patient P, as well as a support element 15 for a second region of the patient, namely his or her head K.

In order to be able to move the head of the patient P into a position which is adapted to the respective examination, or which is comfortable to the patient P, the support element 15 (which is made of a material with a weak attenuating effect with respect to X-radiation, for instance carbon fiber reinforced plastic (CFRP) or wood) can be displaced relative to the support portion 14, namely using an adjusting mechanism 16, which is provided on the side of the support element 15 that faces away from the support portion 14 in the case of the inventive support device 8.

This arrangement of the adjusting mechanism 16 eliminates the possibility of X-ray images that are generated of a patient P who is situated on the support plate 7, be they X-ray shadow images or tomograms, could be diminished in their diagnostic value owing to the presence of the adjusting mechanism 16, since the adjusting mechanism 16 is arranged such that an imaging of the adjusting mechanism 16 in X-ray shadow images or tomograms is not possible. As a result of the described arrangement of the adjusting mechanism 16, the occurrence of artefacts in tomograms is also highly unlikely.

Figure 2:
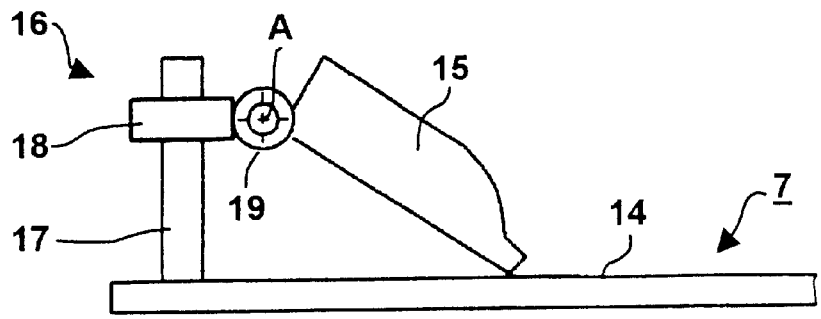
FIG. 2 shows the adjusting mechanism of the inventive support device in an enlarged representation.

As can be seen from FIG. 2, the adjusting mechanism 16 has a bar 17 which is permanently attached to the support plate 7 and is oriented essentially perpendicularly to the surface of the support plate 7, in particular its support portion 14. A sleeve or bushing 18 is guided on the bar 17 in such a way that its height can be adjusted, and the support element 15 is attached at the sleeve 18 by means of a joint 19 in such a way that it can be pivoted around an axis (referenced A in FIG. 2) extending transverse to the longitudinal axis of the support plate 7 and perpendicular to the plane of the drawing.

It is thus also clear that the bar 17, the sleeve 18 and the joint 19 form a push-pivot joint that can be pushed on the bar 17 for the purpose of adjusting the height of the support element 15 and that connects the support element 15 to the bar 17 for the purpose of adjusting the inclination of the support element 15 relative to the support portion 14 of the support plate 7.

Figure 3:
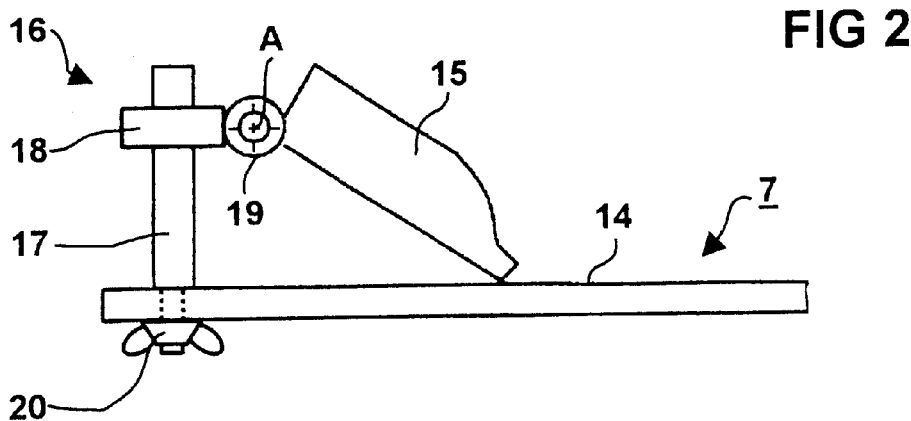
FIGS. 3 and 4 show variants of the inventive support devices in an analogous representation to FIG. 2.

As can be seen from FIG. 3, the possibility also exists to detach the adjusting unit 16 including the support element 15 from the support plate in that a detachable fixing of the bar 17 at the support plate 7 is provided, which is indicated in FIG. 3 by a wing nut 20 which serves for fixing the bar 17 at the support plate 7.

Figure 4:
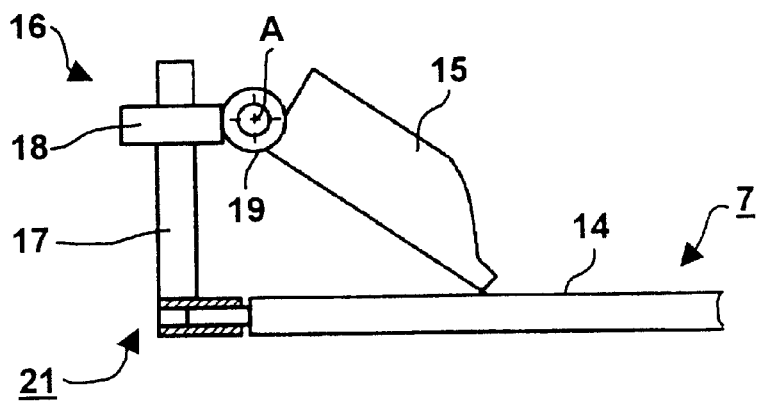

Alternatively, it is also possible to provide a plug connection 21 as in FIG. 4, which allows a detachable connection of the adjusting mechanism 16 and the support element 15 to the support plate 7. In the exemplary embodiment as illustrated in FIG. 4, the support plate 7 is provided with pegs at the end adjacent the bar 17, which engage in corresponding bores in a counterpart that is connected to the bar 17, whereby only one bore and one peg are shown in FIG. 4.

In the exemplary embodiments, the invention is described in connection with a CT system. Inventive support devices may also be used in other diagnostic radiography systems, however. Likewise, the use of the inventive support device is not limited to medical purposes.

The adjusting mechanisms represented in connection with the described exemplifying embodiments are only exemplary. The import and advantage of the invention is that the adjusting mechanism is arranged on the side of the support element that faces away from the portion of he support plate that is provided for accepting the first region of the examination subject.

Although modifications and changes may be suggested by those skilled in the art, it is the intention of the inventor to embody within the patent warranted hereon all changes and modifications as reasonably and properly come within the scope of his contribution to the art.

I claim as my invention:

1. A patient support for a diagnostic radiography system, said patient support comprising:

a support plate having a portion adapted for supporting a first region of an examination subject on said support plate;

a support element having a surface adapted for supporting a second region of said subject, said support element having a first side facing away from said portion of said support plate that is adapted for supporting said first region of said examination subject and a second side facing said portion, with said surface disposed between said first side and said second side; and a mechanical connection connecting said support element to said support plate, and including an adjusting mechanism, disposed exclusively at said first side of said support element facing away from said portion of said support plate, for selectively positioning said support element relative to said support plate, said mechanical connection being disposed to allow a radiological image of said second region of said subject to be obtained in which said mechanical connection is not present.

2. A patient support as claimed in claim 1 wherein said support has a longitudinal axis, and wherein said adjustment mechanism allows pivoting of said support element relative to said support plate around an axis proceeding substantially transversely to said longitudinal axis.

3. A patient support as claimed in claim 1 wherein said mechanical connection comprises a permanent connection between said support element and said support plate.

4. A patient support as claimed in claim 1 wherein said mechanical connection comprises a detachable connection between said support element and said support plate.

5. A patient support as claimed in claim 4 wherein said mechanical connection comprises a plug connection.

6. A patient support as claimed in claim 1 wherein said adjustment mechanism comprises a joint for adjusting an inclination of said support element relative to said support plate.

7. A patient support as claimed in claim 1 wherein said adjustment mechanism comprises a mechanism for adjusting a height of said support element relative to said support plate.

8. A patient support as claimed in claim 1 wherein said adjustment mechanism allows adjusting of an inclination and a height of said support element relative to said support plate, and wherein said adjustment mechanism comprises a push-pivot joint and a carrier proceeding substantially perpendicularly to said support plate, said push-pivot joint being displaceable relative to said carrier for adjusting said height and being pivotable relative to said carrier for adjusting said inclination.

9. A patient support as claimed in claim 1 wherein said portion of said support plate adapted for supporting said first region of said examination subject is adapted to support a body of said examination subject, and wherein said support element is adapted to support a head of said examination subject.

* * * * *